(12) United States Patent
Lal et al.

(10) Patent No.: US 7,484,560 B2
(45) Date of Patent: Feb. 3, 2009

(54) PROCESS FOR ENHANCED RECOVERY OF CRUDE OIL FROM OIL WELLS USING NOVEL MICROBIAL CONSORTIUM

(75) Inventors: Banwari Lal, New Delhi (IN); Mula Ramajaneya Varaprasada Reddy, New Delhi (IN); Anil Agnihotri, Gujarat (IN); Ashok Kumar, Gujarat (IN); Munish Prasad Sarbhai, Gujarat (IN); Nimmi Singh, Gujarat (IN); Raj Karan Khurana, Gujarat (IN); Shinben Kishen Khazanchi, Gujarat (IN); Tilak Ram Misra, Gujarat (IN)

(73) Assignees: The Energy and Resource Institute, New Delhi (IN); Institute of Reservoir Studies, Gujarat (IN)

( * ) Notice: Subject to any disclaimer, the term of this patent is extended or adjusted under 35 U.S.C. 154(b) by 206 days.

(21) Appl. No.: 10/564,365

(22) PCT Filed: Jul. 14, 2004

(86) PCT No.: PCT/IN2004/000206
§ 371 (c)(1),
(2), (4) Date: Jun. 2, 2006

(87) PCT Pub. No.: WO2005/005773
PCT Pub. Date: Jan. 20, 2005

(65) Prior Publication Data
US 2007/0092930 A1    Apr. 26, 2007

(30) Foreign Application Priority Data
Jul. 14, 2003 (IN) .......................... 892/DEL/2003

(51) Int. Cl.
 E21B 43/22   (2006.01)
 C12P 1/00    (2006.01)
 C12N 1/20    (2006.01)
(52) U.S. Cl. ........................ 166/246; 435/41; 435/252.4
(58) Field of Classification Search ........................ None
See application file for complete search history.

(56) References Cited

U.S. PATENT DOCUMENTS 4,057,510 A    11/1977   Crouch et al.

FOREIGN PATENT DOCUMENTS

WO      WO-02/103157 A1    12/2002

OTHER PUBLICATIONS

Bryant RS, Stepp A K, Bertus KM, Burchfield TE, Dennis M (1993) Microbial Enhanced waterflooding field pilots. Devel Petrol Sci 39: 289-306.
Hlitzman DO Petroleum microbiology and the history of its role in enhanced oil recovery, In: Proceedings of the International Confernece on Microbial Enhancement of Oil Recovery. (E.C. Donaldson and J.B. Clarke, eds.) pp. 162-218. Technology Transfer Branch, U.S. Department of Energy, Bartlesville, OK, undated.
Jenneman G.E. et. al., Identification, characterization and application of sulfide-oxidizing bacteria in oilfields; Microbial Biosystem: New Frontiers, 1999 by Atlantic Canadian Society for Microbial Ecology, Halifax Canada, 1999.
Knapp RM, McInerney MJ, Coates JD, Menzie DE, Bhupathiraju VK (1992) Design and implementation of a microbally enhanced oil recovery field pilot, Payne Count, Microbial Ecology of Oil Fields Oklahoma. SPE 24818. Presented at the 1992 Annual Technical Conference and Exhibition, Dallas, TX.
Lazar I. Debrota S. Stefanescu MC, Sandulescu, L, Paduraru R, Stefanescu M, MEOR, recent field trials in Romania: reservoir selection, type of inoculums, protocol for well treatment and line monitoring. Devel Petrol Sci 39:265-288 (1993).
Lin S-C, Minton MA, Sharma MM, Georgiou G (1994) Structural and immunological characterization of a biosurfactant produced by *Bacillus licheniformis* JF-2. Appl Environ Microbiol 60: 31-38.
McInerney M J, Javaheri M., Nagle DP Jr. (1990) Properties of the biosurfactant produced by *Bacillus licheniformis* strain JF-2. J Indust Microbiol 5: 95-102.
Michael J. McInerney, Roy M.Knapp, Use of Indeigenous or Injected Microorganisms for Enhanced Oil Recovery, Microbial Biosystem: New Frontiers, 1999 by Atlantic Canadian Society for Microbial Ecology, Halifax Canada, 1999.
Neslson L. Schneider DR (1993) Six years of paraffin control and enhanced oil recovery with Microbial Product, Para-BacTM. Devel Petrol Sci 39 355-362.

(Continued)

Primary Examiner—Zakiya W. Bates
(74) Attorney, Agent, or Firm—Birch, Stewart, Kolasch & Birch LLP

(57) ABSTRACT

The present invention provides a microbial consortium containing three hyperthermophilic, barophilic, acidogenic, anaerobic bacterial strains for enhanced oil recovery from oil reservoirs where temperatures range from 70° C. to 90√ C. The said microbial consortium is unique in producing a variety of metabolic products mainly $CO_2$, methane, biosurfactant, volatile fatty acids and alcohols in the presence of specially designed nutrient medium. These metabolic products increase sweep efficiency of crude oil from oil bearing poles of rock formation. The present invention also provides a process for enhancing the oil recovery by in situ application of the said microbial consortium.

19 Claims, No Drawings

OTHER PUBLICATIONS

Portwood JT (1995) A commercial microbial enhanced oil recovery process: statistical evaluation of a multi-project database, In: The Fifth International Conference on Microbial Enhanced Oil Recovery and Related Biotechnology for Solving Environmental Problems (R. S. Bryant and L K Sublette eds.). pp. 51-46. Office of Scientific and Technical Information. CONF-9509173.

Raiders RA, Knapp RM, McInerney MJ (1989). Microbial selective plugging and enhaced oil recovery, J Indust Microbial 4: 215-230.

Streeb LP, Brown FG (1992) MEOR-Altamount/Bluebell field project. PE 24334. Presented at the SPE Rocky Mountain Regional Meeting, Casper, Wyoming.

Telang AJ, Ebert S, Foght JM, Westlake DWS, Jenneman GE, Gevertz D, Voordouw G (1997) Effect of nitrate injection on the microbial community in an oil field as monitored by reverse genome probing. Appl. Environ Microbiol vol. 63: 1785-1793.

M., D. Lungerhausen, H. Murtada, and G. Rosenthal. 1995. Development and applicatoin of a new biotechnology of molasses in-situ method: detailed evaluation for selected wells in the Romashkino carbonate reservoir. In: The Fifth International Conference on Microbial Enhanced Oil Recovery and Related Biotechnology for Solving Environmental Problems (R. S. Bryant and K.L. Sublette. eds.), pp. 153-174. Office of Scientific and Technical Information, CONF-9509173.

Raiders RA, McInerney MJ, Revus DE, Torbati HM, Knapp RM Jenneman GE (1986) Selectivity and depth of Microbial plugging in Berea sanstone cores. J. Industrial Microbiol: 195-203.

PROCESS FOR ENHANCED RECOVERY OF CRUDE OIL FROM OIL WELLS USING NOVEL MICROBIAL CONSORTIUM

TECHNICAL FIELD

The present invention relates to a process of enhancing the recovery of crude oil from oil wells using novel microbial consortium MTCC S2-001, proliferated in nutrient mediums I and II. The present invention particularly relates to the use of a mixed microbial strains having anaerobic, barophilic, hyper thermophilic property, wherein said microbial consortium used in situ referred as "MMMAP" (Multi-strain Mixed Microbial Application), for enhancement of crude oil recovery from oil wells.

BACKGROUND AND PRIOR ART REFERENCE

There is a strong relationship between continued industrialization coupled with economic growth and an increase in the demand for oil, especially for the fuel. The demand for crude oil has exceeded the existing production in India and over and above has been demanding more imports, thereby increasing the reliance on those countries that supply oil. The existing conventional oil production technologies are able to recover only about one-third of the oil originally in place in a reservoir.

Crude oil in oil wells, the original oil in place (OOIP), is present in the oil formation rock which may be carbonate or sand stone. The OOIP is generally pushed up on to the ground with the existing overpressures as primary recovery process. The pressure in the oil well drops with the time and there is a need to create overpressure with other means like water injection or non-inflammable gas for secondary recovery of the OOIP. The choice of a specific secondary recovery technique depends on the specifics of the hydrocarbon accumulation. Water injection or waterflooding is the most common secondary recovery technique. In waterflooding, pressurized water is injected into the oil-bearing formation rock and oil is displaced by water and thus oil is recovered from neighboring crude oil producing oil wells. First crude oil, and subsequently crude oil and water are recovered from the production oil well. The remaining oil in place is enormously large in quantity and a suitable tertiary method of its recovery is the need of hour. However, even after secondary recovery, a significant portion of crude oil (more than 60%) remains in the formation, in some cases up to 75% of the original crude oil in place. The fraction of unrecoverable crude oil is typically highest for heavy oils, tar, and complex formations. In large oil fields, more than a billion barrels of oil can be left after conventional water flooding into oil wells. Much of this remaining oil is in micro-traps due to capillary forces or adsorbed onto mineral surfaces (irreducible oil saturation) as well as bypassed oil within the rock formation. A good number of tertiary recovery processes have been proposed.

Recovery of oil by reducing the viscosity and increasing the overpressures of the oil well is one approach to increase the mobility of oil and there by enhance the oil recovery. In yet another approach, the water with pressure will have increased sweep efficiency due to reduced surface tension in the presence of alkline medium or surfactants. In situ combustion of oil/gas present in the well by pumping oxygen or air, however the concept of the in situ combustion does not result a uniform pressurization and mobilization of the oil. One enhanced oil recovery technique uses microorganisms such as bacteria to dislodge the micro-trapped or adsorbed oil from the rock. The goal of this technique, which is known as microbial enhanced oil recovery (MEOR), is to increase oil recovery of the original subsurface hydrocarbons. MEOR processes typically use microorganisms to: (1) alter the permeability of the subterranean formation, (2) produce biosurfactants which decrease surface and interfacial tensions, (3) mediate changes in wettability, (4) produce polymers which facilitate mobility of petroleum, (5) produce low molecular weight acids which cause rock dissolution, and (6) generate gases (predominantly $CO_2$) that increase formation pressure and reduce oil viscosity. Of all, microbial enhanced oil recovery (MEOR) is presently the most preferred approach, where the use of microorganisms such as bacteria produces certain metabolic products that alter the oil properties and thus facilitate to dislodge the oil adhering to the formation rock. Numerous microorganisms have been proposed for achieving various microbial objectives in subterranean formations. Most MEOR techniques involve injection and establishment of an exogenous microbial population into the oil-bearing formation. The population is supplied with nutrients and mineral salts as additives to the water flood used for secondary oil recovery. The development of exogenous microorganisms has been limited by the conditions that prevail in the formation. Physical constraints, such as the small and variable formation pore sizes together with the high temperature, salinity and pressure of fluids in the formation and the low concentration of oxygen in the formation waters severely limit the types and number of microorganisms that can be injected and thrive in the formation. Biological constraints, such as competition from indigenous microbes and the stress of changing environments (from surface to subsurface) also act to limit the viability of exogenous microorganisms. To overcome these problems, indigenous microorganisms, commonly anaerobic, have been proposed in MEOR projects.

There are bacterial systems like the one described in U.S. Pat. No. 2,907,389 uses oil as a carbon source to produce biosurfactants in the presence of oxygen. The oil shale when pumped as oil bearing rock aqueous slurry and treated thus. However this is used in the case of unconsolidated rock formations only. There aerobic and anaerobic categories in MEOR methods. Aerobic system of MEOR as described in U.S. Pat. No. 3,332,487 and anaerobic bacterial system as described in WO 89/10463 and mix of aerobic and anaerobic bacterial system as described in U.S. Pat. No. 5,492,828.

The oil information normally is under anaerobic conditions and the anaerobic bacterial strains will be there as endogenous microbes that may be of useful for facilitating the oil recovery. A the same time exogenously added microorganisms that can use oil as sole source of carbon or that may be requiring a carbon source for growth as described in U.S. Pat. No. 5,492,828 where mixed cultures of aerobic anaerobic bacteria which use crude oil as sole source of carbon source were used for enhanced oil recovery.

New technologies for recovering this residual oil offers the most timely and cost effective solution to reverse the decline in domestic oil production and to increase the oil reserves of the state. Microbial based oil recovery process is one of such methodologies and has several unique advantages that make it an economically attractive alternative to other processes for enhanced oil recovery. This process does not consume large amounts of energy, as do thermal recovery processes and they do not depend on the price of crude oil, as is the case with many chemical recovery processes. Because microbial growth occurs at exponential rates, it should be possible to produce large amounts of useful products quickly from inexpensive and renewable resources. Economic analysis of some MEOR (Microbial Enhanced Oil Recovery) field trials showed that MEOR based oil recovery has produced oil for as little as three dollars per barrel [Knapp et al., 1992; Bryant et al. 1993].

The MEOR processes can be categorized into three main domains depending on the type of production problem and where the process occurs in the reservoir [Jenneman, 1998]. The much talked-about well bore clean out processes involve the use of hydrocarbon-degrading or scale-removing bacteria to remove deposits from tubing, rods, and other surfaces in the well and thereby avoiding frequent chemical treatments to maintain oil production. It greatly reduces operating costs and extends the lifetime of the well [Raiders et al. 1989]. This approach is a mature commercial technology with thousands of wells treated on a regular basis [McInerney et al. 1985; Nelson and Schneider, 1993). The next MEOR technology is well stimulation where an oil well close to its economic limit is treated with a mixture of anaerobic bacteria and a fermentable carbohydrate, usually molasses [Hitzman, 1983]. The production of acids, solvents, and gases in the well bore region is believed to alter the oil/rock characteristics and improve the drainage of oil into the well.

Microbial enhanced water flooding processes are done late in the course of a water flood and involve the injection of nutrients and or microorganisms into the reservoir in order to stimulate microbial activity throughout the reservoir. In carbonate formations, the production of organic acids by the microbial fermentation of carbohydrates is believed to alter pore structure due to the dissolution of the carbonate minerals and substantial improvements in oil production have been reported with this process [Knapp et al., 1992; Wagner et al., 1995]. A method of microbial enhanced oil recovery using oil as sole source of carbon for the enhancing endogenous biomass using specific nutrients, wherein the biomass thus produced will dissociate the oil from the rock, was described in Patent application No WO 01/33040 A1. In sandstone formations, substantial increase in oil production require that the interfacial tension between the oil and water phases be reduced by a factor of 10,000 or more in order to release the oil that is entrapped in small pores by capillary pressure. The lipopeptide biosurfactant produced by Bacillus licheniformis strain JF-2 substantially reduces the interfacial tension between oil and water [Lazar et al., 1993; Lin et al., 1994]. The introduction of this organism along with other anaerobic bacteria in two field trials in Oklahoma has increased oil production and decreased the water to oil ratio of the produced fluids [Bryant et al., 1993]. The addition of nitrate and/or inhibitors of sulfate reduction to injection waters are also used to control hydrogen sulfide production and improve oil recovery [Telang et al., 1997; Streeb and Brown, 1992].

In addition to the above approaches, a microbial plugging process to reduce permeability variation in oil reservoirs in order to improve the performance of water flood was developed [McInerney et al., 1990; McInerney et al., 1999]. The injection water preferentially flows through the most permeable layers of the rock with little or no movement in the less permeable regions. The oil present in the low permeable regions is by-passed and unrecovered. The stimulation of the growth of indigenous microorganisms in the high permeability regions by nutrient injection reduces water movement in these regions and diverts fluid flow into the less permeable regions of the reservoir that have high oil saturation. Laboratory experiments have shown that in situ microbial growth substantially reduces the permeability of sandstone cores, that microbial growth occurs preferentially in the high permeability regions, and that plugging of the high permeability regions diverts fluid flow into less permeable regions [Portwood, 1995; Raiders et al., 1986]. The invention is related to a bacteria and its use in a Microbial Enhanced Oil Recovery (MEOR) process. Bacteria are injected downhole in a petroleum reservoir to modify its profile. This bacterium has the capability to plug the zones of higher permeability within the reservoir so that a subsequent waterflood may selectively enter the oil bearing less permeable zones. The injected water is used to drive this oil to an area where it may then be recovered as described in U.S. Pat. No. 4,799,545. Since the process does not require the production of a specific chemical or the growth of a specific organism, it should be applicable in many reservoirs.

MEOR methods take advantage of the ability of microbes to produce products for improving oil recovery as described in U.S. Pat. No. 4,971,151 where endogenous populations are increased suitable non-glucose containing carbon source which enhances the surface active properties of the endogenous cultures. These products, in turn, can change oil/rock properties in a positive direction, and thus facilitate additional oil recovery. To be successful, microbes must be able to live and proliferate to the expected level in the harsh reservoir environment. In natural conditions the non-conducive and nutrient limiting conditions play a very important role in keeping the ecological balances of the population system. To stimulate the successions of desirable organisms there is need to modify such environments through introduction of specific and selective nutrients or to introduce the desirable populations or through suppression of non-desirable populations. In any of these cases the criteria to be followed, of course with certain exceptions, would be (1) salinity less than 15% NaCl; (2) temperature less than 180° F.; (3) depth less than 8,000 ft; (4) trace elements (As, Se, Ni, Hg) less than 10-15 ppm; (5) permeability greater than 50 md; (6) oil gravity greater than 15° API; and (7) residual oil saturation greater than 25%. There are many inventions on the MEOR technology using either aerobic or anaerobic or a mixture of both, however, a microbial consortium to work under the conditions stated above has not been reported yet.

In the earlier MEOR methods, the microorganism(s) could not survive at a temperature beyond 70° C. The above draw back was overcome by providing a unique combination of novel indigenous micro-organisms and specifically designed nutrient media along with gradual adaptation of the microbes to the required temperatures in the oil wells. The microorganism(s) were found to be highly active even at 90° C. The medium supports the growth and proliferation of the culture in extreme conditions. The metabolic products produced by consuming these nutrients protect the microbes. The composition of the nutrients also promotes selectively the bacterial growth of the consortium of the present invention. In addition, the use of formation water provides appropriate concentration of salts in the nutrient medium and the absence of anaerobic bacteria which are harmful to oil reservoirs is avoided. Also, formation water used is compatible with oil reservoir and helps in the growth of multi bacterial strain or consortia of the present invention.

OBJECTS OF THE INVENTION

The main object of the present invention is to provide a process for enhancing the oil recovery from oil wells using a microbial consortium.

Another object of the invention is to provide a microbial consortium which can withstand higher temperature say up to 90° C. in the oil wells.

Another object of the invention is to provide a microbial consortium comprising microbes having thermophilic, barophillic, acidogenic and anaerobic characteristics.

The another object of the present invention is to provide for a microbial consortium comprising of anaerobic bacteria selected from the group consisting of *Thermoanaerobacterium* sp., *Thermotoga* sp. and *Thermococcus* sp.

Another object of the present invention is to provide a microbial process for reducing viscosity of oil by the production of gases and alteration in the rock characteristics through production of volatile fatty acids in order to enhance oil recovery.

Still another object of the present invention is to provide a stimulating nutritional medium for promoting the growth of the hither to applied microbial consortium to proliferate and continue to grow in the oil well after its application for longer periods.

Yet another object of the invention is to provide nutrient mediums for selective mass scale production of said population of the microbial consortium in the laboratory and further proliferation of the hither to applied microbial consortium in the oil-well.

SUMMARY OF THE INVENTION

Accordingly the present invention relates to enhancement of oil recovery from the oil wells by applying a microbial consortium proliferated in specifically designed nutrient media. The present invention also relates to a process of enhancing the recovery of crude oil from oil wells using novel microbial consortium deposited with the Institute of Microbial Technology, Sector 39-A, Chandigargh 160 036 (Union Territory) having accession no MTCC No. S2-001. The microbial consortium has been isolated from a sample of formation water of an oil well located at Sobhasan, Mehasana Gujarat, India.

The present invention particularly relates to use of a microbial consortium comprising hyperthermophilic, barophilic, acidogenic, and anaerobic microbes for in situ application process hither to called MMMAP (multistrain mixed microbial application process), for enhancement of crude oil recovery from oil wells. The invention also relates to production of volatile fatty acids leading to alteration in rock characteristics thereby enhancing the oil recovery from the oil wells.

DETAILED DESCRIPTION OF INVENTION

The present invention provides for a process for enhancing the oil recovery from oil wells by proliferation of microbial consortium at a temperature up to 90° C., the said process comprising steps of:

a) inoculating the microbial consortium wherein the said consortium having accession no MTCC S2-001 deposited with Institute of Microbial Technology, in a nutrient medium I in the presence of an anaerobic gas mixture of $N_2$, $CO_2$, $H_2$;

b) incubating the microbial consortium of step(a) at a temperature up to 90° C. to obtain seed population of microbial consortium;

c) inoculating microbial consortium of step (b) under aseptic condition in to a nutrient medium II to obtain a biological solution;

d) injecting the biological solution of step (c) in to the oil well, followed by injecting water into the oil well to push the entire biological solution in to the pores of the oil well, allowing the microbial consortium to proliferate which dissociates the oil, and e) obtaining the enhanced oil recovery from oil wells.

The invention further provides a process wherein the said microbial consortium comprises of thermophilic barophilic, acidogenic and anaerobic bacteria. The invention also provides a process wherein the said microbial consortium comprises of anaerobic bacteria selected from the group consisting of *Thermoanaerobacterium* sp., *Thermotoga* sp. and *Thermococcus* sp.

In an embodiment of the present invention provides a process, wherein the nutrient medium I used comprises of:

|  | Quantity/Liter |
|---|---|
| Mineral nutrients |  |
| $MgSO4 \cdot 7H2O$ | 0.5 to 1.5 g |
| $K_2HPO_4$ | 0.4 to 0.6 g |
| $KH_2PO_4$ | 0.1 to 0.6 g |
| Nitrogenous substrates |  |
| $NH_4Cl$ | 0.5 to 1.5 g |
| Yeast extract | 1.0 to 4.0 g |
| Tryptone | 0.5 to 1.0 g |
| Reducing agents |  |
| Cystein HCL | 1.0 to 5.0 g |
| $Na_2S \cdot 9H_2O$ | 2.0 to 5.0 |
| Carbon Source |  |
| Molasses | 50.0 to 100 g |
| Corn steep liquor | 50.0 to 100 g |
| Buffering agent |  |
| $NaHCO_3$ | 1.0 to 2.5 g |
| Vitamin stock solution | 10 to 20 ml |
| Trace mineral stock solution | 15 to 20 ml |

In another embodiment of the present invention provides a process, wherein the nutrient medium II used comprises of:

|  | Quantity/Liter |
|---|---|
| Mineral nutrients |  |
| $MgSO_4 \cdot 7H_2O$ | 0.05 to 0.15 g |
| $K_2HPO_4$ | 0.2 to 0.4 g |
| $KH_2PO_4$ | 0.2 to 0.4 g |
| Nitrogenous substrates |  |
| $NH_4Cl$ | 0.5 to 1.5 g |
| Reducing agents |  |
| Cystein HCL | 0.1 to 0.5 g |
| $Na_2S \cdot 9H_2O$ | 0.1 to 0.5 g |
| Carbon Source |  |
| Molasses | 15.0 to 30.0 g |
| Corn steep liquor | 50-100 g |
| Buffering agent |  |
| $NaHCO_3$ | 1.0 to 2.5 g |
| Vitamin stock solution | 5 to 10 ml |
| Trace mineral stock solution | 5 to 10 ml |

Another embodiment of the present invention provides a process, wherein the trace mineral solution of nutrient media I and II having a pH in the range of 6.50 to 7.50 comprises of:

| Chemicals | Quantity per liter |
|---|---|
| Nitrilotriacetic acid (sodium salt) | 0.82 to 2.00 g |
| $MgSO_4$ | 2.5 to 3.2 g |
| $MnSO_4 \cdot 2H_2O$ | 0.2 to 0.8 g |

-continued

| Chemicals | Quantity per liter |
| --- | --- |
| NaCl | 0.7 to 1.2 g |
| $FeSO_4 \cdot 7H_2O$ | 0.05 to 0.12 g |
| $CoCl_2/CoSO_4$ | 0.07 to 0.14 g |
| $ZnSO_4$ | 0.08 to 0.12 g |
| $CuSO_4 5H_2O$ | 0.008 to 0.015 g |
| $AlK (SO_4)_2$ | 0.007 to 0.015 g |
| $H_3BO_3$ | 0.009 to 0.012 g |
| $Na_2MoO_4 \cdot 2H_2O$ | 0.008 to 0.13 g |

Still another embodiment of the present invention provides a process, wherein the vitamin solution of nutrient media I and II having a pH in the range of 6.50 to 7.50 comprises of:

| Vitamin | Quantity mg/l |
| --- | --- |
| Biotin | 1.2 to 2.2 |
| Folic acid | 1.7 to 2.4 |
| Pyridoxine HCl | 7.0 to 12.0 |
| Thamine HCl | 7.0 to 12.0 |
| Riboflavin | 6.0 to 7.0 |
| Nicotinic acid | 4.0 to 6.0 |
| DL-Calcium Pentothenate | 3.0 to 6.2 |
| P-Aminobenzoic acid | 4.1 to 5.6 |
| Vitaminin $B_{12}$ | 0.08 to 13.0 |
| Lipoic acid | 2.8 to 5.4 |

Yet another embodiment of the present invention provides a process, wherein the incubation temperature and proliferation temperature of the microbial consortium are in the range of 70 to 90° C.

Yet another embodiment of the present invention provides a process, wherein the oil recovery using the said microbial consortia is enhanced by three folds.

Yet another embodiment of the present invention provides a process, wherein the microbial consortium produces biosurfactants which act to reduce surface tension between oil and rock surface dissociate the oil.

Yet another embodiment of the present invention provides a process, wherein the microbial consortium produces carbon dioxide and methane which create localize pressure in core rock pores and thus help in sweeping the oil from the oil well.

Yet another embodiment of the present invention provides a process, wherein the microbial consortium produces volatile fatty acids which solubilise the rock surface and thus dislocate from oil bearing pores. Yet another embodiment of the present invention provides a process where the microbial consortium produced alcohol in oil reservoir which act to reduce the viscosity of crude oil in the oil well.

Still another embodiment of the present invention provides a process, wherein the nutrient medium I is prepared by dissolving mineral nutrients, nitrogenous substances, reducing agents, buffering agent, carbon source and trace mineral in water, adjusting the pH in the range 7.0 to 7.5; autoclaving the solution at a temperature in the range of 120°-125° C., at a pressure of 15-20 psi for a time period of 20-25 minutes; maintaining the temperature of the solution up to 90° C., adding vitamin solution and adjusting the pH to 6.50 to 8.50 using an alkali to obtain nutrient medium.

Still another embodiment of the present invention provides a process, wherein the nutrient medium II is prepared by dissolving mineral nutrients, nitrogenous substances, reducing agents, buffering agent, carbon source and trace mineral in formation water, adjusting the pH in the range 7.0 to 7.5; autoclaving the solution at a temperature in the range of 120°-125° C., at a pressure of 15-20 psi for a time period of 20-25 minutes; maintaining the temperature of the solution up to 90° C., adding vitamin solution and adjusting the pH to 6.50 to 8.50 using an alkali to obtain nutrient medium.

In yet another embodiment of the invention provides a process, wherein to adjust pH 6.50 to 8.50 of the nutrient medium I and II the alkali used is selected from a group consisting of sodium hydroxide and potassium hydroxide.

Yet another embodiment of the present invention provides a microbial consortium adapted for enhancing oil recovery from oil wells having accession no MTCC S2-001, wherein the said microbial consortium comprises of anaerobic bacteria selected from the group consisting of *Thermoanaerobacterium* sp., *Thermotoga* sp. and *Thermococcus* sp.

The process of this invention uses thermophilic, barophilic, anaerobic microbial consortium with the accession no. MTCC S2-001 along with specifically designed anaerobic nutrient medium for in situ application in the oil wells for microbial enhanced oil recovery. The said consortium with the accession number MTCC S2-001 produces metabolic products mainly carbon dioxide, methane, volatile fatty acids, alcohols and biosurfactant in the oil well that enhances sweep efficiency of crude oil from oil bearing rock formation thus increases the oil recovery from the oil well.

Development of Thermophilic, Barophilic and Anaerobic Microbial Consortium for Microbial Enhanced Oil Recovery Collection of oil well formation fluid for development of thermophilic, barophilic anaerobic indigenous microbial consortia: The oil well formation fluid samples for the development of anaerobic, thermophilic, halophilic and barophilic, anaerobic consortia are collected from selected oil wells, from Mehasana Region of Gujarat, India. The formation fluid samples are collected under strict anaerobic conditions following the standard anaerobic sample collection techniques known to the people skilled in the art. For initial observation of microbial populations in the formation fluid, the microorganisms are preferably concentrated by filtration, centrifugation and microscopic observation. The biomass of the indigenous microbial population will typically be a very small fraction of the formation fluid sample's volume. Alternatively, the indigenous microorganisms can be first cultured in the laboratory using techniques familiar to those skilled in the art and then concentrated and collected. Microorganisms' population is amplified to facilitate detection using conventional microbial detection techniques, which are familiar to those skilled in the art.

The formation fluid samples are obtained by sampling procedures that are known to those skilled in the art. Normally, a formation fluid sample is retrieved from the oil formation through oil well tubing or from an open-hole test. Samples from the formation fluid of the selected oil wells whose temperatures are in the range of 70° C. to 90° C. are collected in five litre carboys after flushing the empty carboy with the natural gas from the oil well or nitrogen gas using a portable nitrogen cylinder. To lower the redox potential and to maintain anerobiosis reducing agents @ 0.5 g/L cysteine.HCl and 0.5 g/L $Na_2S.9H_2O$ are added to the sample collected in carboys. The formation fluid samples are used as seed inoculum @ 10% (v/v) for on the spot inoculation into 100 ml anaerobic. serum vials containing the specifically designed anaerobic nutrient medium using a sterile gas tight 10 ml glass syringe. The oil formation fluid samples and the inoculated 100 ml anaerobic serum vials with the said medium are constantly maintained at high temperature in an insulated box during transportation to the lab for processing and are incubated at the desired temperatures (70, 80, 85 and 90° C.) for enrichment and further screening for selecting the most efficient consortium. The formation fluid samples collected as said above with all the precautions known to the people skilled in the art and liquid samples are immediately transferred into an anaerobic chamber and then inoculated @ of 10 ml (v/v) into specifically designed anaerobic nutrient medium prepared in 100 ml serum vials, with different carbon sources and nutrient additions like electron acceptors and growth stimulants, using sterile air tight 10 ml glass syringes. The anaerobic 100 mL serum vials used for media preparation and inoculation are kept under required temperature in incubators at initially at 70° C. and they are subsequently exposed to higher temperatures of upto 90° C. Sub culturing is done at regular intervals of 15 days and every time the samples are analyzed for the production of volatile fatty acids, carbon dioxide, methane, alcohols and biosurfactants are used for assaying bioactive properties using standard protocols known to the people skilled in the art and as described below.

Preparation of Anaerobic Liquid Media for the Development of Thermophilic, Barophilic Anaerobic Microbial Consortium:

For preparation of anaerobic liquid media, all the ingredients of the medium, except thermolabile and reducing agents are dissolved after the other nutrients are added and the medium is boiled and the boiling medium is cooled down. One ml of 0.1% Resazurin as redox indicator is added to one litre of specifically designed anaerobic nutrient medium. The medium is cooled under oxygen free $N_2$. At this stage, reducing agents are added and pH of the medium is adjusted to 8.3. Completion of anaerobiosis was observed by disappearance of Resazurin color in the medium. This reduced medium is dispensed in 100 ml serum vials pre-gassed with desired gas (nitrogen) or a mix of desired gases in desired quantities. The bottles are sealed with butyl rubber stoppers and aluminum caps using a crimper. The bottles are autoclaved at 121° C. for 20 minutes.

Enrichment of the Thermophilic, Barophilic Anaerobic Microbial Consortia;

Well-mixed inoculum sample is drawn anaerobically in a sterile gas tight syringe. The sample @ 10% (v/v) is used for enrichment of bacterial population. The formation fluid samples brought from oil wells are inoculated into specifically designed anaerobic nutrient medium for enrichment of different microbial consortia at 70, 80, 85 and 90° C. The presence of carbon dioxide, methane, fatty acids, alcohols and biosurfactant activities reportedly observed during the incubation time of the cultures are indicative of the microbial growth in the specifically designed anaerobic nutrient medium. Consortia are transferred for further enrichment into a fresh specifically designed anaerobic nutrient medium when carbon dioxide content ranged between 7-10% (v/v).

All the formation fluid samples collected from the selected oil wells for enrichment and development of anaerobic consortia at high temperature and further screening for selecting the most efficient consortium are incubated at different temperatures viz., 70, 80, 85, and 90° C. These formation fluid samples from different selected oil well are maintained in the laboratory under strict anaerobiosis using prescribes standard anaerobic techniques known to the people skilled in the art. The samples are constantly maintained at desired high temperatures in incubators for use as seed inoculum during the process of adaptation and enrichment for the subsequent transfers into fresh medium.

Start-Up for Adaptation and Enrichment of Thermophilic, Barophilic Anaerobic Microbial Consortium:

The samples collected from different sites are used as basic seeding inoculum for start-up of the adaptation and enrichment process. Well-mixed inoculum sample is drawn anaerobically in a sterile gas tight syringe. The sample inoculum @ 10% (v/v) is used for inoculation of bacterial population initially at 70° C. for two cycles and then separately and sequentially at different temperatures viz., 70, 80, 85, and 90° C. as discussed earlier. The adaptation and enrichment of the collected samples is done on specifically designed anaerobic nutrient medium with different carbon sources such as glucose and molasses at experimental temperatures. The consortia are constantly maintained at desired temperatures ranging from 70° C. to 90° C. Analysis of metabolic products at regular intervals is done following the methods known to the people skilled in the art and as described below.

Volatile fatty acids (VFA) production by the developed thermophilic, barophilic anaerobic microbial consortia:

One milliliter of the liquid broth from actively growing enrichment cultures is collected from the 100 ml anaerobic serum vials and centrifuged at 10000 rpm for 10 minutes and filtered through a 0.45 micron membrane filter. The filtrate is then acidified with 50 micro litres of orthophosphoric acid and centrifuged further at 10000 rpm for 10 minutes. The clear supernatant after collecting into fresh Eppendorf tubes is used for analysis of volatile fatty acids using a gas chromatograph fitted with Chromosorb 101 column to FID (Flame ionization detector). The oven, injector and detector temperatures are set at 70° C., 180° C. and 220° C. respectively, with Nitrogen as carrier gas at a flow rate of 20 mL per minute. The peaks are identified based on the standard peak retention times. An aliquot of 2 microlitres of the sample is injected into the column for analysis.

Production of Alcohols by the Developed Thermophilic, Barophilic Anaerobic Microbial Consortium:

In the same way alcohols are detected using a Gas Chromatograph fitted with FID) detector and J&W BB WAX ETR 1237364 column, with oven temperature kept initially at 40° C. with a ramp of 10° C. per minute and to 230° C., and a hold at 230° C. for 5 minutes. The injector and detector temperatures are kept at 250° C. and 250° C. respectively. The carrier gas Helium is used at a flow rate of 5 mL/minute. The peaks are identified based on the retention times of the standard alcohols under the above given conditions of gas chromatography. One milliliter of the liquid broth from actively growing enrichment cultures is collected from the anaerobic vials and centrifuged at 10000 rpm for 10 minutes and filtered through a 0.45 micron membrane filter and 2 microlitres of the sample is injected into the column for analysis.

Production of Methane and Carbon Dioxide by the Developed Thermophilic, Barophilic Anaerobic Microbial Consortium:

The conversion of organic substrates to carbon dioxide and methane requires the active participation of microbial activity resulting the methane and carbon dioxide. The gases produced during the growth of the enrichment cultures in the anaerobic vials are analyzed using Gas Chromatograph fitted with TCD (Thermal Conductivity Detector) and Poropak Q column (80/100 mesh) with oven temperature kept at 35° C. with temperature ramp of 5° C. per minute to 80° C. and 2 minutes hold at 80° C. The injector temperature is kept at 100° C. and detector temperature is 100° C. A volume of 0.2 ml of overhead space gas is taken and injected for analyzing the gaseous composition of the over head space gas in the anaerobic culture vial. The gases are identified based on the retention time values of standard gases of carbon dioxide and methane.

Production of Biosurfactants by the Developed Thermophilic, Barophilic Anaerobic Microbial Consortium:

The biosurfactant activity of the growing enrichment culture for both the culture and supernatant is assayed using actively growing culture broth. The cell bound and soluble biosurfactant activities are analysed. Whole cells harvested from one milliliter of the culture is resuspended in one milliliter of fresh nutrient medium and transferred into a glass test tube. To this 100 microlitres of crude oil is added and the test tube is vortexed for one minute. The glass test tube is kept still for 5 minutes and the increase in turbidity and micelle formation is analyzed spectrophotometrically at 610 nm against a media blank vortexed and processed similarly with crude oil. The biosurfactant activity of the culture broth is also assayed similarly.

Reduction in pH During the Growth of the Developed Thermophilic, Barophilic Anaerobic Microbial Consortium:

The pH of the medium during growth of thermophilic, barophilic anaerobic consortia is measured using a calibrated Orion pH meter.

Selection of the Efficient Thermophilic, Barophilic Anaerobic Microbial Consortium for MEOR Applications From the three oil well formation fluid samples collected for enrichment of microbial systems for MEOR application, three mixed microbial strains (consortia) are obtained. The efficiency of the three consortia in terms of production of said metabolic products for MEOR applications is studied. In the process of enrichment, the three consortia developed through the techniques known to the people skilled in the art, are tested for the production of fatty acids, alcohols, carbon dioxide, methane and providing surface active compounds. The three consortia are studied for the said features at 90° C. and three consortia TERI-MEORJ1, TERI-MEOR J2 and a consortium with accession no. MTCC S2-001 are selected for further studies. It is found after detailed study at this point the consortia TERI MEOR-J1, TERI-MEOR J2 and the consortium with accession no. MTCC S2-001 are suitable for initial sand packed column studies. All the three consortia are tested for their stability at higher temperatures ranging from 70° C. to 90° C. and their performance to produce the said metabolic products useful in MEOR and known to be useful to the people skilled in the art, is studied.

Adaptation of Microbes to Higher Temperatures:

Specifically designed anaerobic nutrient medium is used for adaptation of isolated microorganisms for higher temperatures. Incubations were carried out at different temperatures (70° C. to 95° C.). through adaptation processes, which makes it possible to adapt microorganisms to different temperatures, the three different consortia MEOR-TERI A, MEOR-TERI B and MEOR-TERI C were developed. The consortium MEOR-TERI B was found to have the three different isolates which later are related to viz., *Thermococcus* sp., *Thermotoga* sp., and *Thermoanaerbacterium* sp., and deposited as a consortium with Institute of Microbial Technology, Chandigarh, India with the Accession Number MTCC-S2-001

To determine growth rates of the selected thermophilic, barophilic and anaerobic strains at different temperatures in specifically designed anaerobic nutrient medium. Anaerobic serum vials of 100 mL capacity with 10 ml specifically designed anaerobic nutrient medium was inoculated with 0±2 mL culture in late exponential phase of growth, and incubated at 75, 80, 85, 90, 95 and 98° C. to obtaining stable test temperatures. Each temperature is tested with all the parameters like salt concentration, pH, different carbon sources and over head gases in parallel experiments. Growth curves at the different temperatures were generated by cooling the 100 ml anaerobic serum vials in cool water bath for 2 min to approximately 50° C. One ml culture broth is withdrawn anaerobically and the growth is tested spectrophotometrically at 600 nm. Each sample is processed in duplicate. Every time the culture broth is observed microscopically for testing the purity of the culture. Determination of maximum temperature for growth of the thermophillic, barophilic anaerobic strains is performed in triplicate at required temperature. This experiment is performed in duplicate and repeated three times. In all cases, cells grown at optimal temperature were used as the inoculum.

The sensitivity to antibiotics is tested at 100 micrograms per milliliter in specifically designed anaerobic nutrient medium. Cells were inoculated at 80° C. in 100 ml serum vials.

Substrate utilization analysis is done in 100 ml anaerobic serum vials containing 40 ml medium. The anaerobic were inoculated with an exponentially growing culture at 1% level of inoculum size incubated at 90° C. All tests were performed in duplicate Uninoculated medium is used as a negative control for each substrate and inoculated specifically designed anaerobic nutrient medium is used as a positive control. Growth is recorded after 5, 10 and 15 days. The ability of the thermophilic, barophilic and anaerobic bacterial strain to use single carbon sources for growth is tested. The specifically designed medium is supplemented with one of the following carbon sources acetate, formate, sucrose and glucose to a final concentration of 0.5% (w/v), while yeast extract, peptone, tryptone, pyruvate, casein hydrolysate, casein Casamino acids, succinate, ethanol, Butanol, butyrate, xylose, glycerol, propionate and acetate were present at a final concentration of 0.2%(w/v). A filter sterilized solution of vitamins (10 ml per litre) (Canganella et al., 1997) is added and $N_2$ gas is used as the headspace gas. Nitrogen sources were tested in the absence of $NH_4Cl$ with different carbon sources at a final concentration of 40 mM added as the carbon and energy source in the specifically designed anaerobic nutrient medium. Urea, thiourea, glutamate and gelatin were all tested at 0.2% (w/v), while $NH_4Cl$ and $KNO_3$ were added at 20 mM to the specifically designed anaerobic nutrient medium. The headspace contained $H_2$ and $CO_2$ (20:80). Autotrophic growth of the isolates under $H_2$ and $CO_2$ (80:20) is tested in the specifically designed anaerobic nutrient medium. To determine the ability of the isolate to grow in the absence of elemental sulfur (S), cells were cultured in specifically designed anaerobic nutrient medium from which sulfur compounds had been omitted. The headspace gas is $N_2$ or $H_2$ and $CO_2$ (20:80) in these experiments and titanium (III) citrate (1 mM final concentration) is used as reducing agent instead of $Na_2S.9H_2O$. Growth is determined by direct cell counts in a given volume of the culture broth.

Enhanced Oil Recovery from Sand Packed Column with the Application of Developed Thermophilic, Barophilic Anaerobic Microbial Consortium Microbial enhanced oil recovery experiments are conducted in three sand packed columns made up of stainless steel (SS). The stainless steel cylinders (15 cm×7 cm), used in the study have three outlets made in the upper lid. One is connected to a pressure gauge while the second is connected to a inlet tubing, which is perforated at regular intervals. The third is the outlet for the release of oil. The entire assembly is placed in a water bath maintained at 90° C. The stainless steel cylinders are filled with sand (100-200 mesh), saturated with water and then a specified amount of crude oil by weight is added at 90° C. After two days of equilibration, water is pumped from the inlet point and the water and oil coming out from the outlet is collected. The water is pumped till no oil is found coming with the water from the out let. The crude oil is extracted and measured gravimetrically. Subsequently the sand packed columns are inoculated with TERI-MEOR J1, TERI-MEOR J2 and the consortium with the accession no. MTCC S2-001 and are grown on glucose or molasses as sole carbon source in specifically designed nutrient medium at 90° C. After 20 days of incubation at 90° C., the sand packed columns are pumped with water at 90° C., the water and oil coming out of the column is collected, and crude oil extracted and then measured gravimetrically.

The microbial enhanced oil recovery trials conducted using the said three different consortia using sand packed columns. With the developed consortia on glucose and molasses as sole carbon sources in specifically designed anaerobic nutrient medium, it is found that with molasses as the sole carbon source the three said consortia gave better Enhanced Oil Recovery performance of about 130 to 200% than with glucose supplied as sole source of carbon. A comparison of the said consortia indicated that TERI- MEOR J1 gave superior results than the consortium TERI-MEOR J2 and consortium with accession number MTCC S2-001 by 50% on glucose and 95% on molasses when supplied as sole carbon source. However, the pathgenecity tests conformed that the TERI- MEOR J1, and TERI-MEOR J2 are pathogenic in nature and hence the consortium with accession no. MTCC S2-001 is found to be suitable for microbial enhanced oil recovery from oil wells and finally selected for large scale application in the said process of MEOR.

Characterization of the Selected Thermophilic, Barophilic and Anaerobic Microbial Consortium with Accession no. MTCC S2-001:

The enriched consortium with accession no MTCC S2-001 is purified using serial dilution method known to the people skilled in the art, with the specifically designed anaerobic nutrient medium. The serial dilutions are made upto $10^8$. An aliquot of 100 microlitres is taken from each dilution and inoculated into Hungate's roll tubes containing 5 ml of specifically designed anaerobic nutrient medium with gelrite gellan as the gelling agent kept at 65° C. in a water bath. Immediately after inoculating the tubes are rolled on ice in a tray and the gelrite medium gets solidified evenly o the inner walls of the Hungate's roll tubes. The roll tubes are incubated at 90° C. for 15 days. After 15 days the bacterial colonies formed are picked and inoculated into fresh specifically designed anaerobic nutrient medium. After growing the selected colonies on the specifically designed anaerobic nutrient medium the cultures were analysed for purity, and morphological characters. After detailed observations three different species were found with different morphological characters in the selected thermophilic, barophilic anaerobic consortium with the accession number MTCC S2-001. The results of the morphological characterization of MTCC-S2 consortium are shown in Table 1. The microscopic observation of the cultures growing on the specifically designed anaerobic nutrient medium in the 100 ml anaerobic serum vials is shown in Table 1.

The growth on different substrates and observed metabolites formed are shown in Table 2, The antibiotic sensitivity profiling of the three isolates of the consortium with accession number MTCC S2-001 are shown in Table 3 The growth on different media for the strains present in the microbial consortium is shown in Table 4.

Gram Staining of Cells of Selected Thermophilic, Barophilic Anaerobic Consortium with the Accession no. MTCC S2-001

Actively growing liquid culture are centrifuged at 10000 rpm for 5 minutes and the supernatant was discarded while the pellet is resuspended in sterile distilled water and a thin smear of this liquid culture is prepared on a clean slide and fixed by gentle heating. The smear is stained with crystal violet for 1 min and the excess stain is gently washed off. A few drops of mordant (Gram's iodine/Lugol's iodine) is put on the smear and is left for 30 sec. The slides are then washed with 90% ethanol, air dried and stained with Safianin solution for 1 min. The slide is again washed with water, air-dried and is observed under light microscope at 100× magnification using oil immersion lenses.

The morphological characters observed under the microscope with oil immersion lenses with a magnification of 100×10 showed the presence of three different types of cells, cocci, small rods and long rods. The cocci are motile while the small rods and long rods are non-motile. The gram staining of the cultures indicated that they are Gram negative cocci, Gram positive long rods and Gram negative small rods in nature. The cocci and small rods found to occur in bunches.

Accession of the Selected Thermophilic, Barophilic and Anaerobic Consortium with Accession no. MTCC S2-001:

The microbial consortium has three strains which are related to the genus *Thermococcus, Thermotoga* and *Thermoanaerbacterium*. The selected thermophilic, barophilic anaerobic consortium with Accession number MTCC S2-001 is deposited at Microbial Type Culture Collection Centre, Institute of Microbial Technology (IMTECH), Chandigarh, India.

Effect of pH on the Performance of the Selected Thermophilic, Barophilic Anaerobic Microbial Consortium with Accession no. MTCC S2-001

Effect of pH on selected consortium with accession number MTCC S2-001 at 90° C. was done by adjusting the pH of specifically designed anaerobic nutrient medium to the required range of 4.0 to 8.5. In the first experiment the pH range kept for the consortium with accession number MTCC S2-001 was 6.0 to 8.5 with increments of 0.5 between the treatments. In the second experiment a more detailed analysis of the effect of pH on the said metabolic products was done maintaining the pH range of the medium at 4.0 to 6.0 with an increment of 0.5. The results indicated that the highest production of metabolites occurred in the specifically designed anaerobic nutrient medium with a pH 8.3. The consortium with accession number MRCC S2-001 showed higher production of said metabolic products when the initial pH was kept at 8.3. When the metabolic product formation peaked the pH dropped to a minimum low of 3.09. The substrate utilization pattern also showed a definite trend during the pH drop and with different pH settings. pH 8.3 gave the best utilization of the substrate and production of said metabolites that are found essential in the present invention Effect of Salt Concentration on the Performance of Selected Thermophilic, Barophilic Anaerobic Microbial Consortium with Accession no. MTCC S2-001:

Effect of salinity on selected with accession number MRCC S2-001 consortium checked using sodium chloride at a concentration of 0.00 to 3.0% (w/v) with an increment of 0.5% between the treatments in the specifically designed anaerobic nutrient medium during two separate sets of experiments. In the first experiment, 0.00 to 2.0% sodium chloride was used in the specifically designed anaerobic nutrient medium. And the Volatile Fatty Acid production was found to be 1200 ppm to 1300 ppm at 0.0 to 1.0% after 360 hours of incubation at 90° C. In the second experiment, a more detailed study on the said metabolite production, and substrate utilization. On both the substrates molasses and glucose the metabolite production was high at all the salt concentrations with the product formation peaking between 100-150 hours of growth. The said consortium with accession no MTCC S2-001 tolerated sodium chloride concentration up to 3.0% w/v. A 40 to 65% substrate utilization when glucose was given as sole substrate of carbon at all concentrations of sodium chloride. The effect of salt on the pH of the medium during the metabolic products formation resulted in a drop of pH from 8.3 to 5.04. In the presence of 0.5% sodium chloride the amount of fatty acid production was between 1200 to 1300 ppm in 360 hours of incubation. The invention thus in its embodiment showed the positive effect of increased sodium chloride concentration in the specifically designed anaerobic nutrient medium.

Preservation and Maintenance of Selected Thermophilic, Barophilic Anaerobic Consortium with Accession no. MTCC S2-001:

A 50% (v/v) glycerol solution is prepared anaerobically. A 50% glycerol (v/v) solution to the final concentration is added anaerobically with the help of air tight sterilized syringe to the liquid culture in the anaerobic serum vials. The culture temperature is reduced gradually to freezing and then stored at −40° C. in deep freezer. A routine check up of the culture viability is carried out every three months.

TABLE 1

Morphological characteristics of the MTCC-S2 consortium

| Parameters | Strain No 1 | Strain No 2 | Strain No 3 |
|---|---|---|---|
| Culture growth | Obligate Anaerobe | Obligate Anaerobe | Obligate Anaerobe |
| Electron acceptors | Nitrate, Sulphur | Nitrate, Sulphur | Nitrate, Sulphur |
| pH | 6.5-8.5 | 6.5-8.5 | 6.5-8.5 |
| Size | | | |
| Radius | 0.5-1.0 microns | 0.1-0.3 | 0.1-0.4 |
| Length | — | 1.5-2.3 microns | 4.5-6.0 microns |
| Area | 3.2-4.0 sq. microns | 0.5 sq. microns | 4.3 sq. microns |
| Perimeter | 6.34 microns | 3.8 microns | 22.4 microns |
| Shape | Coccii | Small rods | Rods |
| Motility | Motile | Non-motile | Non-motile |
| Flagella | Tufted Polar Flagellated | -Nil- | -Nil- |
| Nutrition | Chemoorganotrophic | Chemoorganotrophic | Chemoorganotrophic |
| Extracellular Structures | No unusual | No unusual | No unusual |
| Sporulaton | Non-sporulating | Non-sporulating | Non-sporulating |
| Gram Reaction | −ve | −ve | +ve |
| Temperature | 85-95° C. Obligately Thermophilic | 85-95° C. Obligately Thermophilic | 85-95° C. Obligately Thermophilic |
| Temperature Optimum | 90° C. | 90° C. | 90° C. |

TABLE 2

Substrate Utilization:

| Substrate | Strain No 1 | Strain No 2 | Strain No 3 |
|---|---|---|---|
| Acetate | + | + | + |
| Formate | + | + | + |
| Glucose | + | + | + |
| Fructose | − | − | − |
| Succinae | + | + | + |
| Glutamate | − | − | − |
| Pyruvate | + | + | + |
| Peptone | + | + | + |
| Tryptone | + | + | + |
| Glycerol | + | + | + |
| Butanol | + | + | + |
| Formate | + | + | + |
| Sucrose | + | − | − |
| Butyrate | − | | |
| Ethanol | + | + | + |
| Xylose | + | − | − |
| Yeast Extract | + | + | + |
| Casaminoacids | − | − | − |
| Casein | − | − | − |
| Lactate | + | + | + |

TABLE 3

Antibiotic Sensitivity:

| Antibiotic (100 ug/mL) | Strain 1 (Cocci) | Strain 2 (Small rods) | Strain 3 (Long rods) |
|---|---|---|---|
| Vancomycin | + | + | + |
| Erythromycin | + | + | + |
| Ampicillin | − | + | + |
| Rifamycin | − | − | − |
| Carbencillin | + | + | + |
| Novobiocin | + | + | + |
| Neomycin | − | + | + |

TABLE 3-continued

Antibiotic Sensitivity:

| Antibiotic (100 ug/mL) | Strain 1 (Cocci) | Strain 2 (Small rods) | Strain 3 (Long rods) |
|---|---|---|---|
| Nalidixic acid | − | − | + |
| Spectinomycin | + | + | + |
| Oxytetracyclin | − | − | − |
| Kanamycin | − | + | + |
| Strptomycin | − | − | − |

All the chemicals are mixed in RO (reverse osmosis) water to 1000 ml with pH adjustment to 7.0-7.5 with 1 N NaOH, and autoclave nutrient mixture at the temperature of around 121±5° C. at the pressure of 15-20 psi for a period of 20-25 minutes, cooling the said mixture containing medium to the well temperature before inoculating the multi-strain mixed microbial population for enrichment.

The mixture of nutrient medium is prepared, by mixing all the components mentioned above except the reducing agents and vitamins in a 2 litre glass flask. The medium in the glass flask is heated to 90° C. in water bath with a temperature regulator set at 90° C. The medium is purged with anaerobic gas mixture comprising of $N_2$; $CO_2$; $H_2$ in a ratio of 80:10:10 and the reducing agents are added. Then medium is dispensed into specialized anaerobic vessels using 50 ml disposable syringe. The vessels are then properly plugged and sealed with rubber stopper and aluminum crimps. Then vessels are autoclaved at 121±5° C. and 15-20 psi pressure for 20-25 minutes. The vessels are removed from the autoclave and transferred immediately to a water bath maintained at 90° C. The vitamin solution is added to the autoclaved nutrient mixture medium and the multi-strain mixed microbial population is inoculated into this medium. The overhead space of the vessels is filled with the anaerobic gas mixture of $N_2$; $CO_2$; $H_2$ in a ratio of 80: 10:10. The inoculated vessels are then incubated at 90° C.

According to this invention, the mass culturing of the multi-strain mixed microbial population is done in a specially designed anaerobic bioreactor of 100 litre capacity with high temperature and pressure controls facilities. In accordance with this invention the nutrient mixture used contains all the components mentioned above and preparation procedure as described above. The medium is prepared in the 100 litre capacity anaerobic bioreactor and autoclaved at 121±5° C. and 15-20 psi for 20-25 minutes. After the sterilization the anaerobic bioreactor is flushed with sterile anaerobic gas mixture comprising $N_2$; $CO_2$; $H_2$ in a ratio of 80:10:10 and vitamin mixture is added. The impeller speed, anaerobic gas purging, pH regulation and temperature controls are set at 30-40 rpm 0.2-0.5 vvm 7.0-7.5 and 80-90° C. respectively. The inoculum thus developed is used for MEOR field test.

The fully grown multi-strain thermophillic, barophilic anaerobic culture is transferred aseptically from bioreactor to specially designed insulated containers with continuous purging of anaerobic gas mixture. The containers are sealed and transported to MMMAP application well site. Total volume of biological solution to be injected depends on the pay zone thickness, porosity, radius of treatment, injectivity etc. As pre-flush, nutrient medium in the quantity 20-30% of total biological solution is pumped into the well. Then 1-2% multi strain anaerobic thermophillic, barophilic culture is added to nutrient medium, blended and pumped into the well, followed by an after flush (nutrient medium only) of about 20% of biological solution. Then a volume of water is injected adequate to displace the entire biological solution through the perforations and into the target reservoir.

The nutrient medium of the present invention provides salts like sodium chloride help in increased salt-bridges in the proteins. $H_2$, $S_2$, $S_2O_3$ serve as electron donors and $Na_3$ ions as electron acceptor. The nitrogenous material helps in the protein synthesis which is important for increased production of induced proteins at higher temperature. The adaptability is achieved by $K^+$ ions, amino acids produced from the nutrients supplied and sugars (which is present at a level of 40% of the total sugars in molasses). Iron, copper, manganese, tungsten etc are used as common enzyme ingredients.

A multi-strain mixed microbial process for microbial enhanced oil recovery from oil wells by reducing viscosity of oil and by increase in sweep efficiency through production of volatile fatty acids and carbon dioxide gas is thus invented and preparation of the process thereof according to a preferred embodiment is herein described in the following example"

Novelty

The novelty of the present invention is to adapt and stabilize the bacterial activity of multi bacterial strain at a high temperature up to 90° C. using specially designed composition of a nutrient media. The media supports the growth and proliferation of multibacterial strain both in laboratory and oil well under extreme conditions. The metabolic products produced protect the microbes. The composition of the nutrients also promotes selectivity of the bacterial growth of the present invention.

In addition, the use of formation water provides an appropriate concentration of salts in the nutrient medium and the absence of anaerobic bacteria which are harmful to oil reservoirs is avoided. Also, formation water used is compatible with oil reservoir and helps in the growth of multi bacterial strain of the present invention.

Another novelty is that the selected thermophilic, barophilic multi bacterial strain do not degrade crude oil in the reservoir hence caloriphilic value of crude oil will not reduce.

The following examples illustrate the invention which should not be construed to limit the scope of the present invention.

EXAMPLES

Example 1

Core flood studies with selected thermophilic, barophilic anaerobic consortium with accession no. MTCC S2-001 in simulating oil well conditions.

The core flood study using consortium with accession no MTCC S2-001 is done to test the feasibility of the in situ application of the consortium with accession no. MTCC S2-001 for enhanced oil recovery. The performance of the said consortium is given in table 5.

During 21 days of incubation of oil containing core at 90 C, and 8.93% incremental recovery of oil by MEOR over water flood and 21.0% residual oil recovery was achieved with the consortium with the accession no MTCC S2-001.

TABLE 5

Experimental details and results on core flood study

| Experimental details | |
|---|---|
| Incubation period | 21 days |
| Core plug used | Barea |

TABLE 5-continued

Experimental details and results on core flood study

| | |
|---|---|
| Length | 19.88 cm |
| Diameter | 3.836 cm |
| Area | 11.523 cm$^2$ |
| Porosity | 19.0% |
| Kair | 148 md |
| Pore volume | 43 CC |
| Oil used | Jotana # 57 |
| Water | With salinity of 20 g of KCL in one liter |
| Temperature | 90 C. |
| Rate of injection | 20 CC/hour |
| Test results | |
| Soi | 65.12% of PV |
| SOR by water flood followed by MEOR flood | 27.9% of PV |
| SORW after incubation and production | 22.1% of PV |
| Oil recovery by water flood | 57.14% |
| Total recovery | 66.07% |
| Incremental recovery by MEOR over water flood | 8.93% |
| % recovery of residual oil | 21.0 |
| % of $CO_2$ in the produced gas | 1.8 |

Example 2

Microbial nutrient mixture, containing NaCl 0.01-0.02% $MgCl_2$. 7 $H_2O$; 0.04-0.06% $K_2HPO_4$; 0.4-0.6% $KH_2PO_4$; 0.1-0.2 Resazurin; 0.1% Cysteine HCl; 0.07% $Na_2S.9H_2O$; 0.1-0.5% $NaHCO_3$ (added separately from a stock of 2%); 0.2-0.5% Vitamin solution (v/v); 1-2% Trace mineral solution; 1-2% Molasses and Corn steep liquor mix; 1.5-2% oil well formation water; 50-60% and then mixed in RO (reverse osmosis) water to 1000 ml adjusting the pH 7.0 to 7.5 and autoclaved the mixture without adding vitamin solution at a temperature of 121° C. and 15-20 psi pressure for 20-25 minutes.

The trace elements solution used for the nutrient mixture is comprising 0.05-0.12% nitrilotriacetic acid; 0.1-0.2% $MnSO_4.2H_2O$; 0.001-0.002% $FeSO_4$; 0.001-0.007% $CaCl_2$; 0.001-0.003% AlK $(SO_4)_2$; 0.001-0.006% $H_3BO_3$; 0.001-0.002% $Na_2MoO_4.2H2O$ The Vitamin solution contained 0.001-0.002% biotin; 0.0001-0.0003% folic acid; 0.01-0.03% pyridoxine-HCl; 0.0001-0.0004% riboflavin; 0.0001-0.0004% thiamine HCl; 0.001-0.0005% nicotinic acid; 0.0001-0.0005% calcium D pantothenate; 0.0001-0.0003% vitamin $B_{12}$; 0.0001-0.0004% PABA; 0.0001-0.0005% lipoic acid. The pH of the mixture is adjusted to. 6.8 with 1.0 N NaOH and the mixture is sterilized aseptically with 0.22µ membrane filter assembly.

The designed nutrient mixture is dispensed hot in specialized anaerobic vessels and reduced while purging with anaerobic gas mix, by adding reducing agents. The vessels are sealed and autoclaved. After autoclaving, the nutrient mixture is kept at 90° C. in a temperature controlled hot water bath. The medium is inoculated with multi-strain mixed microbial population selected from a group consisting of *Thermoanaerobacterium* sp., *Thermotoga* sp. and *Thermococcus* sp. to prepare the inoculum ready for scale up or mass production of the same for in situ application process MMMAP.

For the application of MMAP in oil wells; the wells were identified on the basis of reservoir and fluid properties viz. permeability>25 md, porosity>20%, salinity of oil associated water up to 10%, ° API of crude oil >15 API, viscosity of oil <30 cp, water cut (coproduced) 30-90%, reservoir temperature up to 90° C. and residual oil saturation minimum >25%

The multi-strain thermophilic anaerobic culture is taansferred aseptically from bioreactor to specially designed insulated containers with continuous purging of anaerobic gas mixture. The containers are sealed and tansported to MMMAP application well site. Total volume of biological solution to be injected depends on the pay zone thickness, porosity radius of treatment, injectivity etc. As pre-flush, nutrient medium in the quantity 20-30% of total biological solution is pumped into the well. Then 1-2% multi strain anaerobic thermophilic culture is added to nutrient medium, blended and pumped, followed by injection of after flush treatment (nutrient medium only). The total biological solution is displaced by volume of water adequate to inject the entire biological solution through the perforations and into the target reservoir. All the injections are made at surface pressure not exceeding hydro fracturing pressure of the formation.

After the application of the MMMAP in oil wells, the oil wells are closed for 20-30 days. The process MMMAP stimulated the microbial growth in situ and produced their metabolic products in particular the carbon dioxide which reduce the viscosity of oil. The end product of the application of MMMAP in oil wells is increased oil recovery up to 3 folds. The multi-strain mixed microbial metabolic products are carbon dioxide and volatile fatty acids which are harmless and which do not adversely affect the oil quality.

Example 3

All conditions used are identical as in example 1 above, except that a combination of any two bacteria are used from the group consisting of *Thermoanaerobacterium* sp., *Thermotoga* sp. and *Thermococcus* sp to provide enhancement of oil recovery up to 0.8 fold.

Example 4

All conditions used are identical as in example 1 above, except that any one bacterium is used from the group consisting of *Thermoanaerobacterium* sp., *Thermotoga* sp. and *Thermococcus* sp., to provide enhancement of oil recovery up to 0.3 fold.

ADVANTAGES OF THE PRESENT INVENTION

1. Provides novel nutrient mediums for the growth of the multi bacterial strain up to a temperature of 90° C.
2. The present invention provides an efficient process for the enhanced oil recovery from oil wells.

REFERENCES CITED

Patent Documents:

| | | |
|---|---|---|
| U.S. Pat. No. 5,492,828 | Premuzic et al., | Feb. 20, 1996 |
| U.S. Pat. No. 5,044,435 | Sperl, et al. | Sep. 3, 1991 |
| U.S. Pat. No. 5,163,510 | Sunde Egil | Nov. 17, 1992 |
| Patent application WO 01/33040 | Torsvik Terje and Sunde Egil | Nov. 3, 2000 |
| U.S. Pat. No. 4,971,151 | Alan Sheehy | Nov. 20, 1990 |
| Patent application WO 89/10463 | | |
| U.S. Pat. No. 3,332,487 | Jones | Sep. 30, 1963 |
| U.S. Pat. No. 2,907,389 | Hitzman, | Jun. 18, 1956 |
| U.S. Pat. No. 4,799,545, | Acheson Willard et al., | Jan. 24, 1989 |
| U.S. Pat. No. 4,905,761 | Bryant | Mar. 6, 1990 |

REFERENCES

1. Bryant R S, Stepp A K, Bertus K M, Burchfield T E, Dennis M (1993) Microbial Enhanced waterflooding field pilots. Devel Petrol Sci 39: 289-306.
2. Hitzman D O (1983) Petroleum microbiology and the history of its role in enhanced oil recovery. In: Proceedings of the International Conference on Microbial Enhancement of Oil Recovery. (E. C. Donaldson and J. B. Clark, eds.) pp. 162-218. Technology Transfer Branch, U.S. Department of Energy, Bartlesville, Okla.
3. Jenneman G E (1988) Identification, characterization and application of sulfide-oxidizing bacteria in oilfields. Microbial Ecol. In press.
4. Knapp R M, McInerney M J, Coates J D, Menzie D E, Bhupathiraju V K (1992) Design and implementation of a microbially enhanced oil recovery field pilot, Payne Count, Microbial Ecology of Oil Fields Oklahoma SPE 24818. Presented at the 1992 Annual Technical Conference and Exhibition, Dallas, Tex.
5. Lazar I, Dobrota S, Stefanescu M C, Sandulescu L, Paduraru R, Stefanescu M (1993) MEOR, recent field trials in Romania: reservoir selection, type of inoculum, protocol for well treatment and line monitoring. Devel Petrol Sci 39: 265-288.
6. Lin S-C, Minton M A, Sharma M M, Georgiou G (1994) Structural and immunological characterization of a biosurfactant produced by *Bacillus licheniformis* JF-2. Appl Environ Microbiol 60: 31-38.
7. McInerney M J, Javaheri M., Nagle D P Jr. (1990) Properties of the biosurfactant produced by *Bacillus licheniformis* strain JF-2. J Indust Microbiol 5: 95-102.
8. McInerney M J, Jenneman G E, Knapp R M, Menzie D E (1985) In situ microbial plugging process for subterranean formations. U.S. Pat. No. 4,558,739.
9. Michael J. McInerney, Roy M. Knapp, John L. Chisholm, Vishvesh K. Bhupathiraju, John D. Coates. 1999.
10. Use of indigenous or injected Microorganisms for Enhanced Oil Recovery In Microbial Biosystems: New Frontiers. Proceedings of the $8^{th}$ International Symposium on Microbial Ecology Bell C R, Brylinksy M, Johnson-Green P (ed) Atlantic Canada Society for Microbial Ecology, Halifax, Canada, 1999.
11. Neslson L, Schneider D R (1993) Six years of paraffin control and enhanced oil recovery with the microbial product, Para-Bac™. Devel Petrol Sci 39: 355-362.
12. Portwood J T (1995) A commercial microbial enhanced oil recovery process: statistical evaluation of a multiproject database, In: The Fifth International Conference on Microbial Enhanced Oil Recovery and Related Biotechnology for Solving Environmental Problems (R. S. Bryant and L K Sublette eds.). pp. 51-76. Office of Scientific and Technical Information. CONF-9509173.
13. Raiders R A, Knapp R M, McInerney M J (1989). Microbial selective plugging and enhanced oil recovery. J Indust Microbial 4: 215-230.
14. Streeb L P, Brown F G (1992) MEOR-Altamount/Bluebell field project. PE 24334. Presented at the SPE Rocky Mountain Regional Meeting, Casper, Wyo.
15. Telang A J, Ebert S, Foght J M, Westlake D W S, Jenneman G E, Gevertz D, Voordouw G (1997) Effect of nitrate injection on the microbial community in an oil field as monitored by reverse genome probing. Appl Environ Microbiol 63z: 1785-1793.
16. Wagner, M., D. Lungerhausen, H. Murtada, and G. Rosenthal. 1995. Development and application of a new biotechnology of molasses in-situ method: detailed evaluation for selected wells in the Romashkino carbonate reservoir. In: The Fifth International Conference on Microbial Enhanced Oil Recovery and Related Biotechnology for Solving Environmental Problems (R. S. Bryant and K. L. Sublette. eds.), pp. 153-174. Office of Scientific and Technical Information, CONF-9509173.
17. Knapp R M, McInerney M J, Coates J D, Menzie D E, Bhupathiraju V K (1992) Design and implementation of microbially enhanced oil recovery field pilot, Payne Count, Microbial Ecology of Oil Fields Oklahoma. SPE 24818. Presented at the 1992 Annual Technical Conference and Exhibition, Dallas, Tex.
18. Lin S-C, Minton M A, Sharma M M, Georgiou G (1994) Structural and immunological characterization of a biosurfactant produced by *Bacillus licheniformis* JF-2. Appl Environ Microbiol 60: 31-38.
19. Raiders R A, McInerney M J, Revus D E, Torbati H M, Knapp R M, Jenneman G E (1986) Selectivity and depth of microbial plugging in Berea sandstone cores. J Indust Microbiol 1: 195-203.

We claim:

1. A process for enhancing the oil recovery from an oil well by proliferation of a microbial consortium at a temperature up to 90° C., the process comprising steps of:
   a) inoculating the microbial consortium having accession no MTCC S2-001, in a nutrient medium I in the presence of an anaerobic gas mixture of $N_2$, $CO_2$, $H_2$;
   b) incubating the microbial consortium of step (a) at a temperature up to 90° C. to obtain seed population of microbial consortium;
   c) inoculating the seed population of the microbial consortium of step (b) under aseptic conditions into a nutrient medium II to obtain a biological solution;
   d) injecting the biological solution of step (c) into the oil well, followed by injecting water into the oil well to push the entire biological solution into the pores of the oil well, allowing the microbial consortium to proliferate and dissociate the oil, and
   e) obtaining enhanced oil recovery from the oil well.

2. The process as claimed in claim 1, wherein said microbial consortium comprises anaerobic bacteria.

3. The process as claimed in claim 1, wherein said microbial consortium comprises anaerobic bacteria selected from the group consisting of *Thermoanaerobacteriumn* species, *Thermotoga* species and *Thermococcus* species.

4. The process as claimed in claim 1, wherein said nutrient medium I comprises mineral nutrients, nitrogenous substrates, reducing agents, carbon source, vitamins and trace minerals.

5. The process as claimed in claim 4, wherein said mineral nutrients comprise $MgSO4,7H2O$, $K_2HPO_4$ and $KH_2PO_4$.

6. The process as claimed in claim 4, wherein said nitrogenous substrates comprise $NH_4Cl$, Yeast extract and Tryptone.

7. The process as claimed in claim 4, wherein said reducing agents comprise cysteine and $Na_2S \cdot 9H_2O$.

8. The process as claimed in claim 4, wherein said carbon source comprises molasses and corn steep liquor.

9. The process as claimed in claim 4, wherein said trace minerals comprises Nitrilotriacetic acid (sodium salt), $MgSO_4$, $MnSO_4 \cdot 2H_2O$, $NaCl$, $FeSO_4 \cdot 7H_2O$, $CoCl_2/CoSO_4$, $ZnSO_4$, $CuSO_4 \cdot 5H_2O$, $AlK(SO_4)_2$, $H_3BO_3$ and $Na2MoO_4 \cdot 2H_2O$.

10. The process as claimed in claim 4, wherein said vitamins comprises Biotin, Folic acid, Pyridoxine HCl, Thiamine HCl, Riboflavin, Nicotinic acid, DL-Calcium Pentothenate, P-Aminobenzoic acid, Vitaminin $B_{12}$ and Lipoic acid.

11. The process as claimed in claim 1, wherein said nutrient medium II comprises mineral nutrients, nitrogenous substrates, reducing agents, carbon source, vitamins and trace minerals.

12. The process as claimed in claim 11, wherein said mineral nutrients comprises $MgSO_4 \cdot 7H_2O$, $K_2HPO_4$ and $KH_2PO_4$.

13. The process as claimed in claim 11, wherein said nitrogenous substrate is $NH_4Cl$.

14. The process as claimed in claim 11, wherein said reducing agents comprises cysteine and $Na_2S \cdot 9H_2O$.

15. The process as claimed in claim 11, wherein said carbon source comprises molasses and corn steep liquor.

16. The process as claimed in claim 11, wherein said trace minerals comprises Nitrilotriacetic acid (sodium salt), $MgSO_4$, $MnSO_4 \cdot 2H_2O$, $NaCl$, $FeSO_4 \cdot 7H_2O$, $CoCl_2/CoSO_4$, $ZnSO_4$, $CuSO_4 \cdot 5H_2O$, $AlK(SO_4)_2$, $H_3BO_3$ and $Na_2MoO_4 \cdot 2H_2O$.

17. The process as claimed in claim 11, wherein said vitamins comprises Biotin, Folic acid, Pyridoxine HCl, Thiamine HCl, Riboflavin, Nicotinic acid, DL-Calcium Pentothenate, P-Aminobenzoic acid, Vitaminin $B_{12}$ and Lipoic acid.

18. A microbial consortium that is deposited under accession no MTCC S2-001.

19. A process for enhancing the oil recovery from an oil well comprising steps of:
   a) injecting a consortium of bacteria cultured from the consortium deposited under accession no. MTCC S2-001 into the oil well, followed by injecting water into the oil well to push the entire biological solution into the pores of the oil well, allowing the microbial consortium to proliferate and dissociate the oil, and
   b) obtaining enhanced oil recovery from the oil well.

* * * * *